United States Patent [19]

Wilms

[11] 4,312,574
[45] Jan. 26, 1982

[54] PHOTOTOPOMETER

[75] Inventor: Karl-Heinz Wilms, Emmering, Fed. Rep. of Germany

[73] Assignee: Optische Werke G. Rodenstock, Munich, Fed. Rep. of Germany

[21] Appl. No.: 10,025

[22] Filed: Feb. 6, 1979

[30] Foreign Application Priority Data

Feb. 7, 1978 [DE] Fed. Rep. of Germany ....... 2805084

[51] Int. Cl.³ .......................... A61B 3/14; A61B 3/10
[52] U.S. Cl. ........................................... 351/7; 351/13
[58] Field of Search ..................................... 351/7, 13

[56] References Cited

U.S. PATENT DOCUMENTS 1,721,208 7/1929 Currier et al. ...................... 351/7 X
1,918,540 7/1933 Hartinger .............................. 351/13
4,159,867 7/1979 Achatz et al. .................... 351/13 X Primary Examiner—John K. Corbin
Assistant Examiner—Rodney B. Bovernick
Attorney, Agent, or Firm—Craig and Antonelli

[57] ABSTRACT

A phototopometer for determining the curvature of the cornea of an eye including pairs of measuring targets arranged in a measuring target carrier for disposition at a predetermined distance from the cornea of the eye to be measured and a photographing system for photographing the measuring targets reflected on the cornea to enable the radius of curvature of the cornea in the zone of the measuring target reflection to be determined from the reproduced image of the measuring targets in accordance with geometrical characteristics the photographing system has an optical axis and the spacing of the measuring targets of each measuring target pair is dimensioned in dependence on the distance thereof to the optical axis of the photographing system and to the cornea, whereby in accordance with the reproduction scale of the photographing system, the spacings of all reproduced measuring target pairs are in the same proportional relationship to the respectively associated radius of the cornea.

16 Claims, 5 Drawing Figures

PHOTOTOPOMETER

The present invention relates to a phototopometer for determining the curvature of the cornea of an eye, wherein measuring targets reflected on the cornea are photographed, and the radius of curvature of the cornea in the zone of the measuring target reflection is determined from the reproduction of the measuring targets, taking into account the geometrical characteristics.

German Patent No. 1,933,815 discloses an apparatus for recording and observing the curvature of the cornea of an eye wherein light passed through a slot is reproduced in the cornea and this image is photographed. By means of an appropriate deflection of the optical beam paths with the aid of mirrors, a curvilinear representation of the cornea curvature is produced. However, a simple numerical determination of the radii of curvature of the cornea in various ranges cannot be executed.

German Patent Application P No. 26 41 004 describes an apparatus and process for measuring the curvature of the cornea, according to which light targets are reflected from the cornea to be measured directly onto detectors, wherein the latter transmit the imaging location of the measuring targets to an electronic computer in the form of electric signals. The computer calculates the radius of curvature of the cornea associated with the location of the light target. However, this arrangement requires a considerable expenditure of electronic devices and reacts with sensitivity to erroneous adjustments.

It is an object of this invention to provide an apparatus for determining the radii of curvature of a cornea simultaneously in various regions thereof, wherein the respective radii of curvature are obtained without the use of conversion tables or electronic computers.

This object is attained according to the present invention by a phototopometer for determining the curvature of the cornea of an eye, wherein measuring targets arranged on a measuring target carrier of the phototopometer and reflected on the cornea are photographed with the radius of curvature in the zone of the measuring target reflection being determined from the reproduction of the measuring targets, taking into account the geometrical characteristics. A number of measuring target pairs are arranged in the measuring target carrier of the phototopometer and disposed at a predetermined distance from the cornea during measurement. The spacing of the measuring targets of each measuring target pair is dimensioned, in dependence on their distance to the optical axis of the photographic system and to the cornea, so that, considering the reproduction scale of the photographic system, the spacings of all reproduced measuring target pairs are in the same proportional relationship to the respectively associated radius of the cornea.

By means of the arrangement of associated measuring target pairs, provided within the scope of this invention, the surprisingly advantageous possibility is obtained of reading off directly the respectively associated radius of curvature of the cornea in the sagittal direction from a photograph of the measuring target pairs imaged or reproduced by way of the cornea, by applying a single, simple measuring scale or device to each of the reproduced measuring target pairs.

The measuring target pairs can be arranged in rows, the images of which appear centrally toward the middle of the cornea. Such a row of measuring targets results, when evaluated, sagittally in curvature cross sections through the cornea. The spacings of the individual measuring targets forming respectively a pair of measuring targets, are different and contain the correction values required by the structural characteristics of the apparatus so that the images of all measuring target pairs can be evaluated with the same measuring scale or device for determining the associated, sagittal radii of curvature.

By changing the reproduction scale in the photographic imaging system, any desired zone of the cornea can be reproduced on an enlarged scale and thus the accuracy of the measurement can be increased. For the specific measurement of lateral zones of the cornea, fixation points can be offered to the eye to be examined, these fixation points lying outside of the optical axis of observation and the photographing optic of the phototopometer. Additional fixation points can be arranged together with the measuring target pairs in a spherical-segment area, the center of curvature of which is located during the examination approximately in the center of curvature of the cornea to be measured.

The measuring target pairs can be constituted by optical fibers terminating in corresponding openings of the spherical-segment area. Light can be supplied to these optical fibers from a source of continuous light, as well as a source of flashing light such as a strobe. The relatively weak continuous light source makes it possible to continuously observe the adjustment and examination procedure, while the source of flashing light serves for producing a high-contrast photograph which can be easily evaluated. For the fixation targets, it is possible to provide light-emitting diodes [LED's] which can be switched independently of the measuring targets. The measuring targets and the fixation targets can also be arranged in an imaging area deviating from the area of a spherical segment, for example, in a planar surface. Of course, this results in a different correction of the spacings of the individual measuring target pairs.

These and further objects, features and advantages of the present invention will become more obvious from the following description when taken in connection with the accompanying drawings which show, for purposes of illustration only, a single embodiment in accordance with the present invention; and wherein FIG. 1 is a longitudinal sectional view along the optical axis of the apparatus of the present invention;

Figure 1:
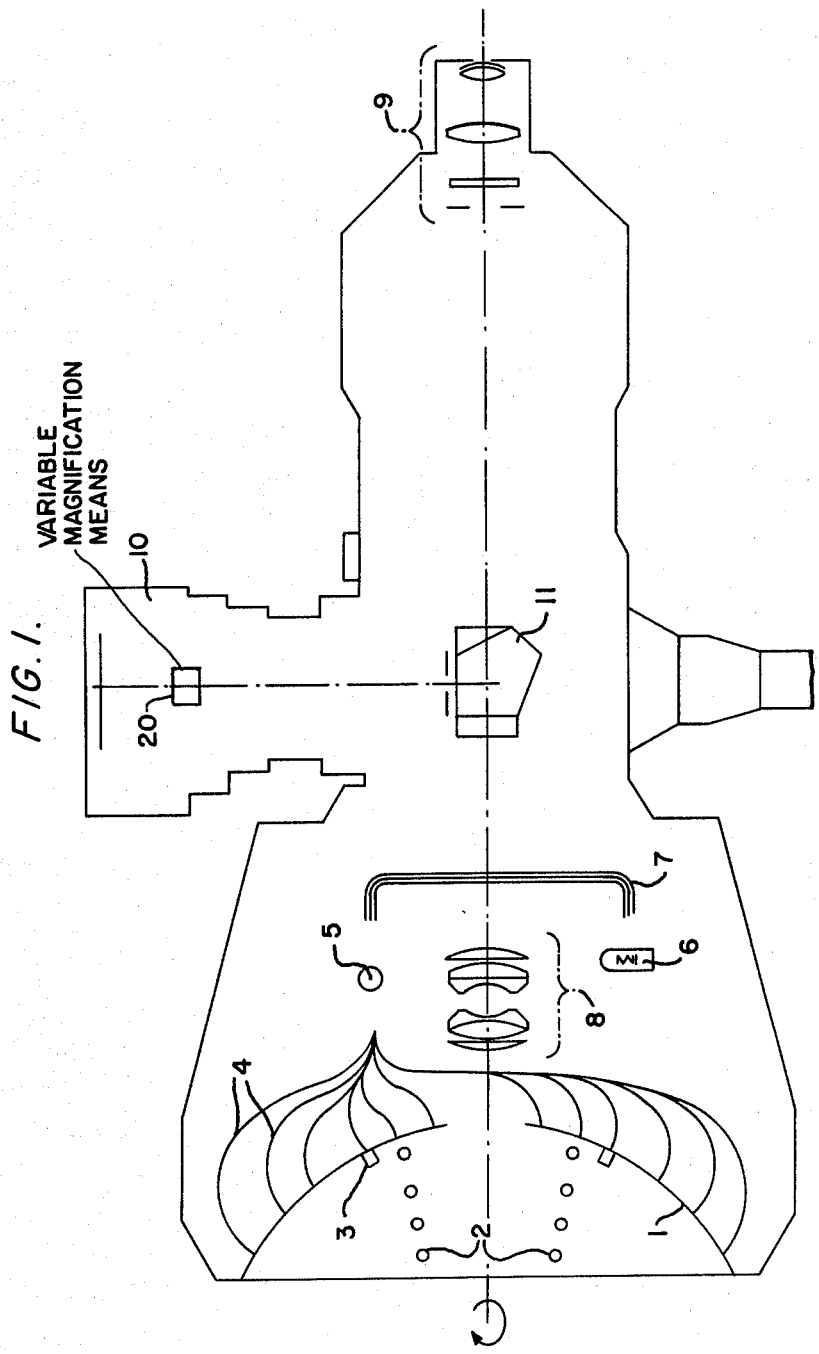

Referring now to the drawings wherein like reference numerals are utilized to designate like parts throughout the several views, there is shown in FIG. 1, longitudinal section through the apparatus of this invention. The apparatus includes a projection surface 1 in the form of a spherical segment and provided with a plurality of measuring targets 2 arranged in pairs as indicated by the lead lines for the reference numeral 2 in FIG. 1, as well as fixation targets 3. The measuring targets 2 consist of the ends of optical fibers 4 which can be supplied with light from a strobe 5 or similar light source as well as from a continuous-light source 6. Light emanating from the light source 6 passes through an optical fiber arrangement 7 via the strobe 5 to the input surfaces of the optical fibers 4. An objective 8 serves for observing measuring target pairs reflected in the cornea with the aid of an ocular 9 as well as for photographing these target pairs with a camera system 10 including a variable magnification means 20, the beam path being divided in a beam-splitting prism 11.

The structural part of the apparatus comprising the projection surface 1 with the optical fibers 4, as well as the fixation targets 3, is detachable and can be made to be exchangeable for another apparatus part with a dimensionally deviating arrangement of the measuring targets 2. The projection surface 1 carrying the measuring targets and fixation targets can be pivoted by at least 45° about the optical axis of the photographic system as represented by the arrow indication.

Figure 2:
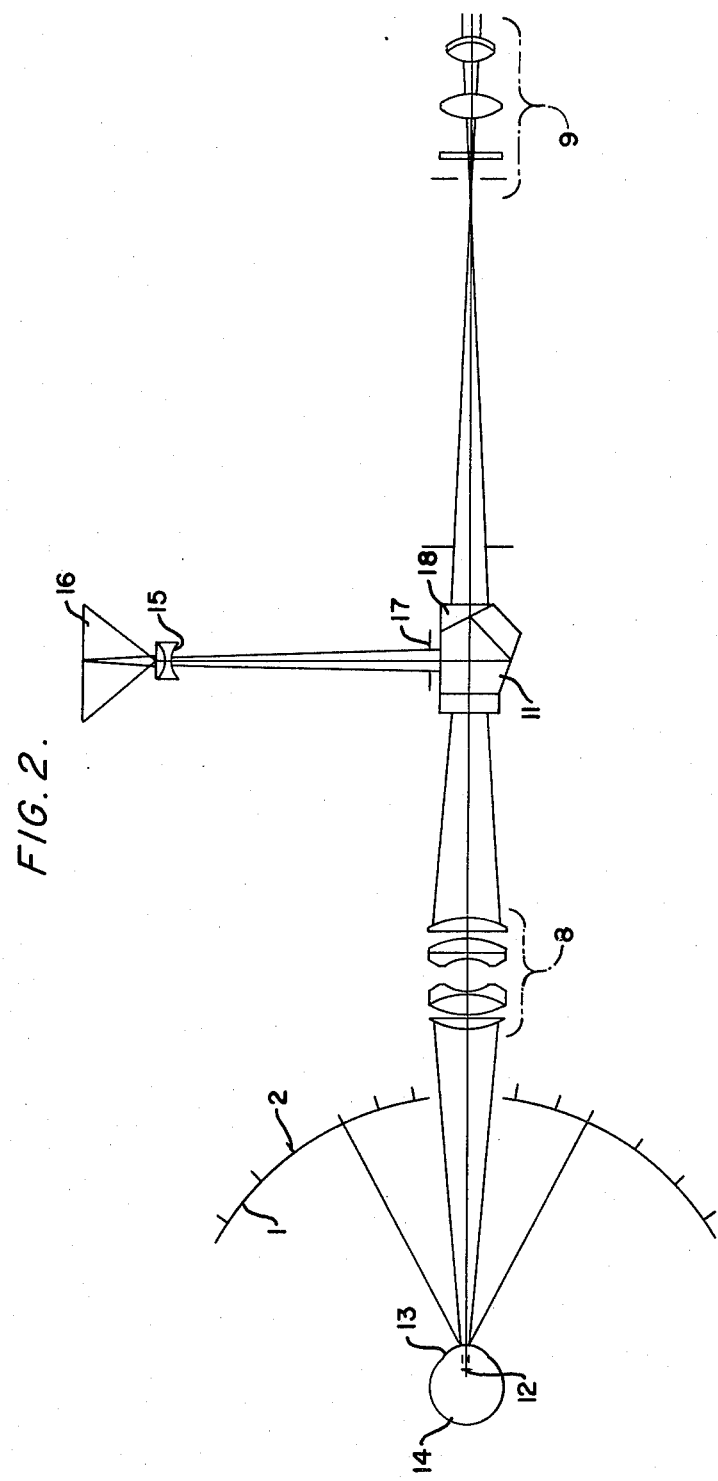
FIG. 2 illustrates the optical beam path within the apparatus.

FIG. 2 shows the optical beam paths within the apparatus illustrated in FIG. 1. The center of curvature 12 of the projection surface 1 is to be maximally congruent with the center of curvature of the cornea 13 of the eye 14 to be measured. The measuring targets 2, arranged in pairs, are reflected by the cornea 13 in the direction toward the objective 8 and pass through the latter with the targets being reproduced via the beam-splitting prism 11 and a negative optical element 15 on the support 16 of a light-sensitive layer of the camera or similar system. For a flawless reproduction of the measuring targets, a diaphragm 17 is arranged behind the beam-splitting prism 11 which diaphragm can be constructed as a click-stop diaphragm disk. The optical system of the photographic system is arranged to provide a reproduction scale of variable magnification.

Figure 3:
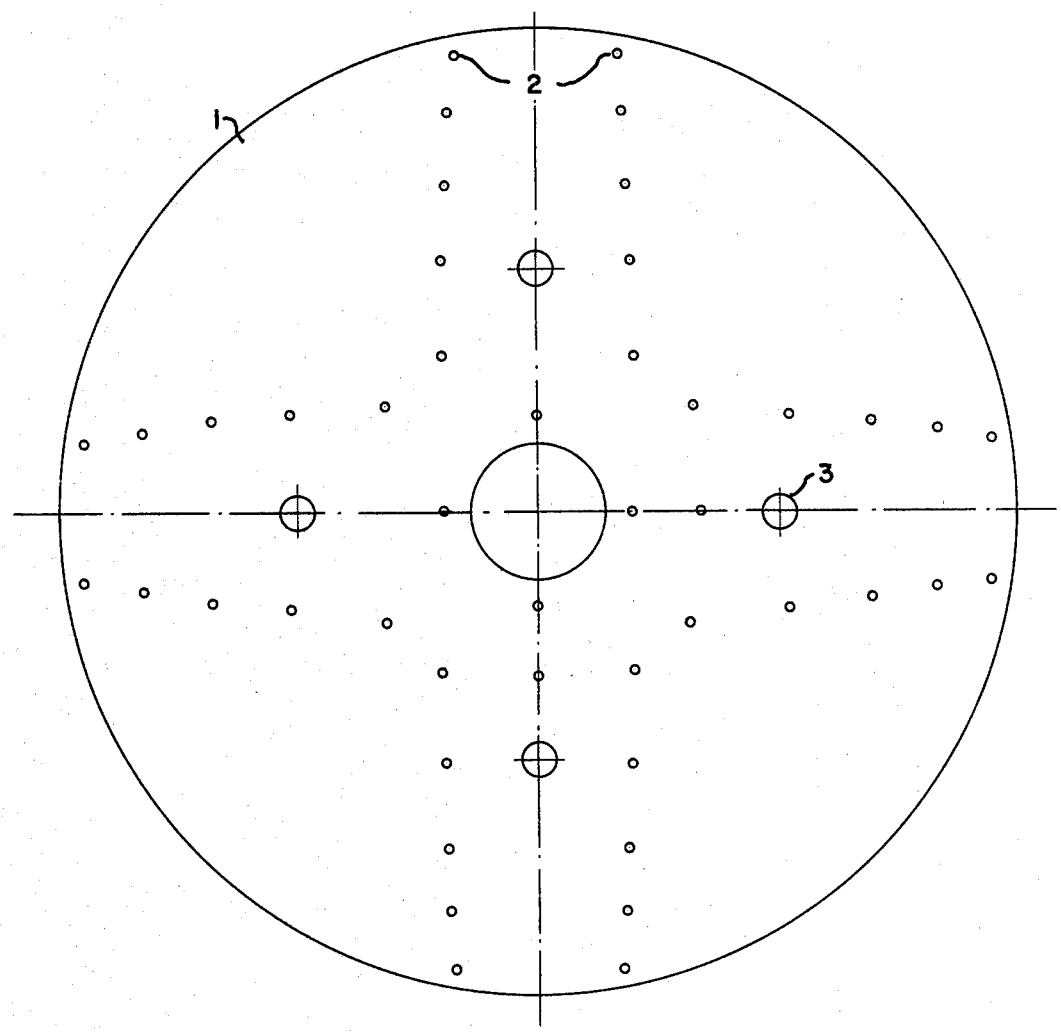
FIG. 3 illustrates the projection surface containing the measuring target pairs as seen in the direction of the optical axis.
Figure 4:
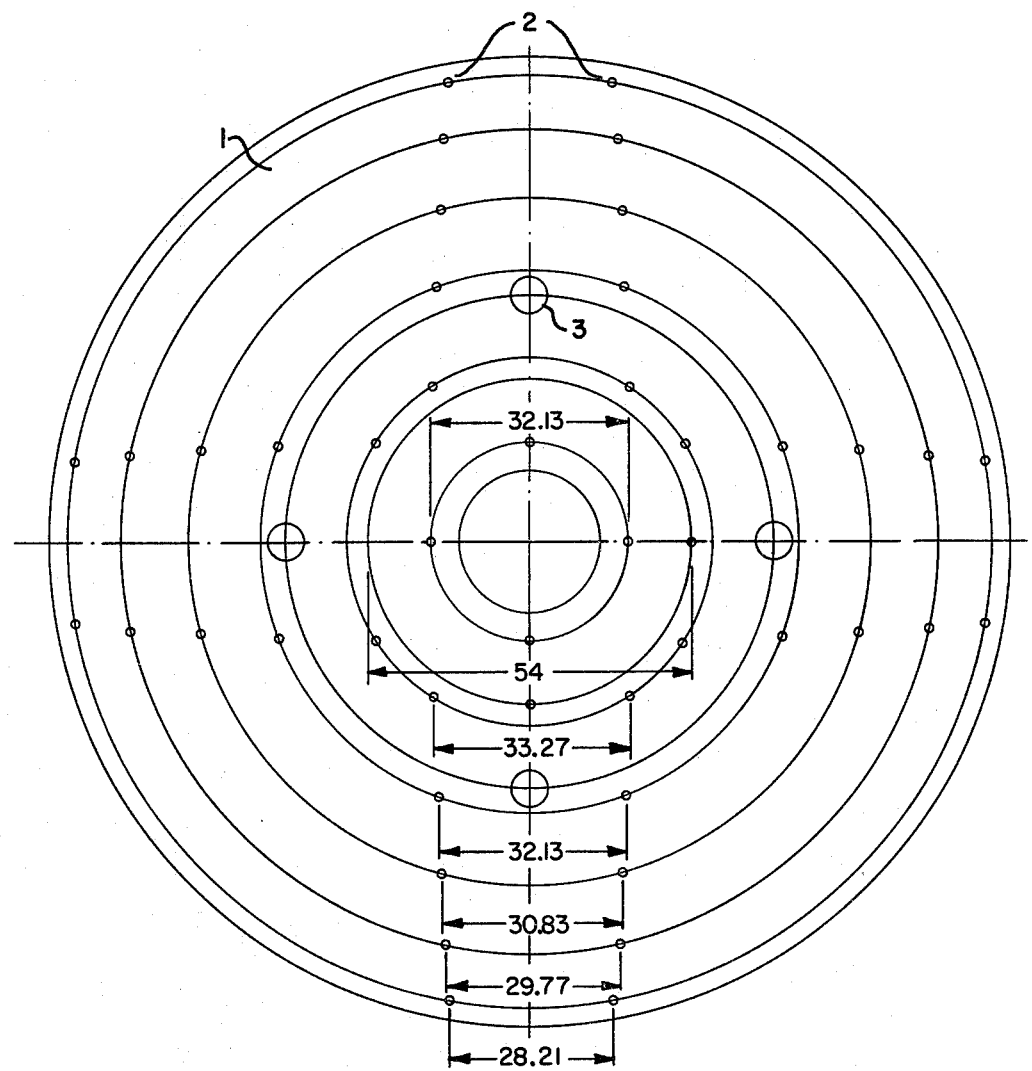
FIG. 4 shows the same view as FIG. 3, but with numerical data of a specific example.

In a selected embodiment, the projection surface 1 has a spherical radius of 90 mm and the objective 8 has a focal length of 80 mm and provides for double magnification. Together with the enlargement effect of the optical element 15, which has a magnification value of 2.5, the measuring target pairs are reproduced in a five-fold enlargement. The measuring targets of each measuring target pair appear, from the center of curvature of the cornea, under the same angle, here 23.5°. This angle yields the positions of the measuring target pairs indicated in FIGS. 4 and 5. As shown in FIGS. 3 and 4, the measuring target pairs are arranged in the form of rows of measuring targets 2 extending at a mutual spacing with the distance between selected pairs of measuring targets being indicated in FIG. 4. Further, as shown, two measuring target groups consisting of respectively two measuring target rows are provided at an angle of 90° with respect to one another in the direction of the radial axes shown in dash-dot line and which groups extend through the optical axis of the photographic system. As shown in FIG. 4, assuming a radius of a respective measuring target pair are arranged the same distance from the optical axis and an opposite side of a common radius, each pair of a group having the same common radius.

The beam-splitting prism 11 comprises a wedge 18 cemented thereto which forms, together with the body of the prism, a partially reflective mirror and yields on the imaging plane 16 an upright and unreversed image. The ocular 9 makes it possible to observe the measuring targets 2 reflected in the cornea 13 prior to, during, and after the photographing operation. An index within the ocular, which can be moved toward the observed pairs of measuring targets, makes it possible, with an appropriate calibration, to directly read off the radii of curvature associated with the individual measuring targets pairs.

FIG. 3 shows the projection surface 1 with the measuring target pairs 2, as well as with additional fixation targets 3 located outside the optical axis in actual size as seen in the direction of the optical axis.

Figure 5:
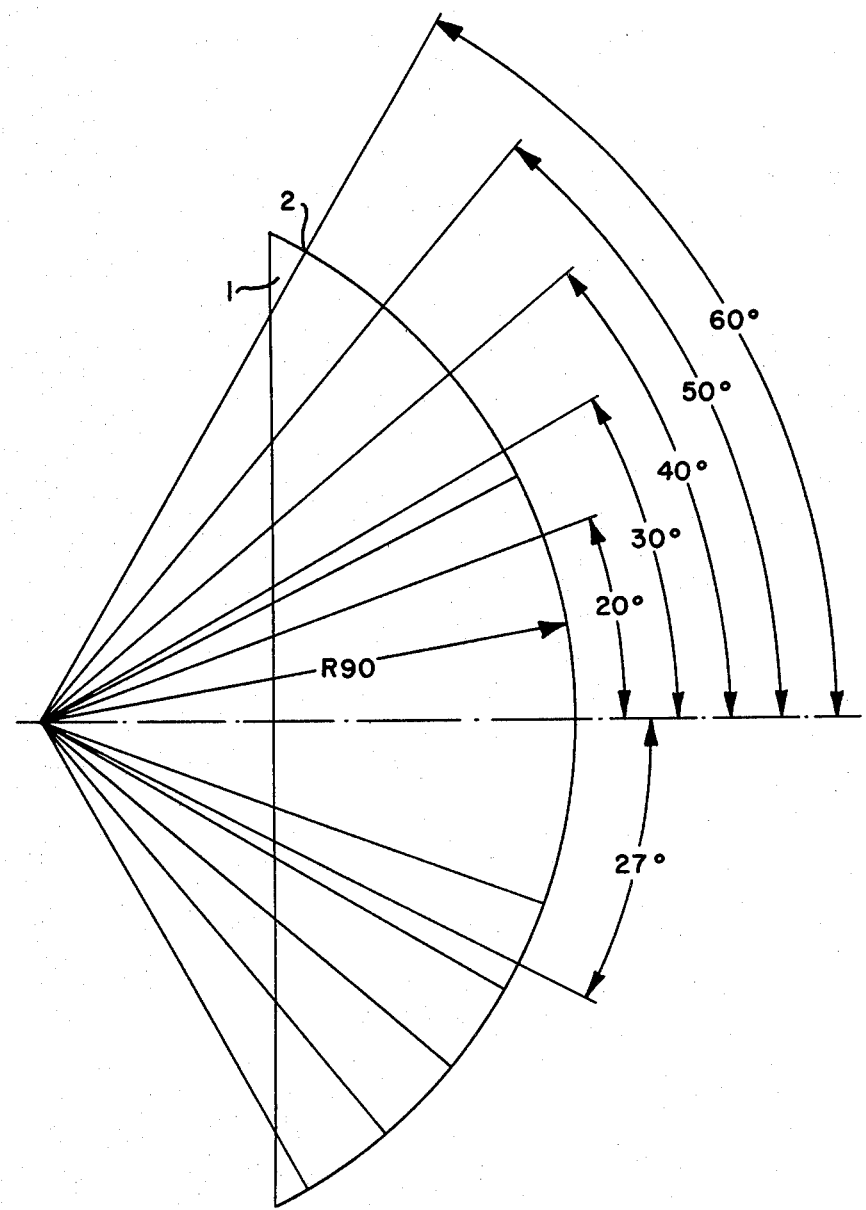
FIG. 5 is a lateral view of FIG. 4.

FIGS. 4 and 5 show the projection surface 1 in an axial view and a lateral view. These figures of the drawings contain dimensional data regarding the positioning of the measuring target pairs based upon a spherical radius R90 (90 mm). The indicated data are correlated with the data for the apparatus illustrated in FIG. 2 with the spacings of the measuring target pairs on the photograph corresponding to the associated radii of curvature in millimeters. As is apparent from the various figures, the measuring targets 2 are arranged on the inside of a spherical segment area of the projection surface 1 wherein the optical axis of the photographic system extends through the center of the spherical segment and the center of curvature of the cornea to be measured is likewise located approximately in this center.

The measuring scale required to evaluate the photograph is not illustrated. This measuring scale may be, for example, an ordinary ruler with millimeter calibration or a ruler having a linear graduation.

While I have shown and described one embodiment in accordance with the present invention, it is understood that the same is not limited thereto but is susceptible of numerous changes and modifications as known to those skilled in the art and I therefore do not wish to be limited to the details shown and described herein but intend to cover all such changes and modifications as are encompassed by the scope of the appended claims.

I claim:

1. A phototopometer comprising a plurality of pairs of measuring targets arranged in a measuring target carrier for disposition at a predetermined distance from the cornea of an eye to be measured, and means for photographing the measuring targets reflected on the cornea to enable the radius of curvature of the cornea in the zone of the measuring target reflection to be determined from the reproduced image of the measuring targets in accordance with geometrical characteristics, the photographing means having an optical axis, the spacing of the measuring targets of each measuring target pair being dimensioned in dependence on the distance thereof to the optical axis of the photographing means and to the cornea, the plurality of measuring target pairs being positioned in the measuring target carrier radially outwardly from the optical axis, the measuring targets of respective measuring target pairs being arranged the same radial distance from the optical axis and on opposite sides of a common radius, whereby in accordance with the reproduction scale of the photographing means, the spacings of all reproduced measuring target pairs are in the same proportional relationship to the respectively associated radius of the cornea so as to enable a determination of the curvature of the cornea from the reproduced spacing of the measuring target pairs.

2. A phototopometer according to claim 1, wherein the measuring target pairs are arranged in rows of measuring targets extending at a mutual spacing in the measuring target carrier.

3. A phototopometer according to claim 2, wherein the measuring target carrier is provided with two measuring target groups arranged at an angle of 90° with respect to each other, each measuring target group including two measuring target rows, each measuring group extending through the optical axis of the photographing means.

4. A phototopometer according to claim 3, wherein the measuring target carrier having the measuring target groups is pivotal about the optical axis of the photographing means by at least 45°.

5. A phototopometer according to claim 1 or 4, wherein the photographing means includes means for providing a reproduction scale of variable magnification.

6. A phototopometer according to claim 1 or 4, further comprising a prism disposed in the beam path of the photographing means for yielding an upright, unreversed image for photographic reproduction.

7. A phototopometer according to claim 6, wherein the prism is a beam-splitting prism providing one beam for the photographing means, the one beam extending at angle to the beam path between the prism and the measuring target carrier and another beam to enable observation of the measuring target pairs reflected in the cornea, the another beam extending in the direction of the beam path between the prism and the measuring target carrier.

8. A phototopometer according to claim 7, wherein the photographing means includes a camera, diaphragm and magnification means along the path of the one beam.

9. A phototopometer according to claim 8, further comprising an ocular disposed along the path of the another beam.

10. A phototopometer according to claim 9, further comprising an objective providing a predetermined magnification disposed along the beam path between the prism and the measuring target carrier.

11. A phototopometer according to claim 1 or 4, wherein the measuring target carrier is provided with a spherical-segment area, the measuring targets being arranged on the interior of the spherical-segment area, the optical axis of the photographing means extending through the center of the spherical-segment area and the center of curvature of the cornea to be measured being disposed proximate to the center of the spherical-segment area.

12. A phototopometer according to claim 11, wherein the measuring targets comprise optical fibers terminating in the spherical-segment area, and at least one light source means for providing a common light source for the optical fibers.

13. A phototopometer according to claim 12, wherein two light source means are provided, one light source means being a continuously illuminating light source, and the other light source means being a flashing light source.

14. A phototopometer according to claim 12, wherein the measuring target carrier is provided with a plurality of fixation targets, the fixation targets being arranged in the spherical-segment area and outside the optical axis of the photographing means.

15. A phototopometer according to claim 14, wherein the fixation targets comprise light-emitting diodes.

16. A phototopometer according to claim 1, wherein the plurality of measuring target pairs are arranged in at least one group having the same common radius, each measuring target pair of the group being arranged at different radial distances from the optical axis, the spacings of the reproduced measuring target pairs enabling determination of a sagittal radius of curvature of the cornea.

* * * * *